United States Patent
Chernov et al.

(10) Patent No.: US 9,265,568 B2
(45) Date of Patent: Feb. 23, 2016

(54) DESTRUCTION OF VESSEL WALLS FOR ENERGY-BASED VESSEL SEALING ENHANCEMENT

(75) Inventors: Boris Chernov, Saint-Petersburg (RU); Nataliya Chernova, legal representative, Saint-Petersburg (RU); Igoris Misuchenko, Saint-Petersburg (RU); Georgy Martsinovskiy, Saint-Petersburg (RU); Mikhail Verbitsky, Stoughton, MA (US)

(73) Assignee: Coviden LP, Mansfield, MA (US)

( * ) Notice: Subject to any disclaimer, the term of this patent is extended or adjusted under 35 U.S.C. 154(b) by 1025 days.

(21) Appl. No.: 13/108,468

(22) Filed: May 16, 2011

(65) Prior Publication Data
US 2012/0296239 A1   Nov. 22, 2012

(51) Int. Cl.
  *A61B 18/14* (2006.01)
  *A61B 17/32* (2006.01)
  *A61B 18/00* (2006.01)

(52) U.S. Cl.
  CPC ..... *A61B 18/1445* (2013.01); *A61B 17/320092* (2013.01); *A61B 2018/0019* (2013.01); *A61B 2018/0063* (2013.01); *A61B 2018/00196* (2013.01); *A61B 2018/00589* (2013.01); *A61B 2018/00595* (2013.01); *A61B 2018/00607* (2013.01); *A61B 2018/00994* (2013.01); *A61B 2018/1412* (2013.01); *A61B 2018/1455* (2013.01)

(58) Field of Classification Search
  CPC .................................................. A61B 18/1402
  USPC ......................................... 606/27, 34, 41, 169
  See application file for complete search history.

(56) References Cited

U.S. PATENT DOCUMENTS

| 3,608,553 | A | * | 9/1971 | Balamuth ..................... 606/131 |
| D249,549 | S | | 9/1978 | Pike |
| D263,020 | S | | 2/1982 | Rau, III |
| D295,893 | S | | 5/1988 | Sharkany et al. |
| D295,894 | S | | 5/1988 | Sharkany et al. |
| D298,353 | S | | 11/1988 | Manno |
| D299,413 | S | | 1/1989 | DeCarolis |
| 4,850,353 | A | | 7/1989 | Stasz et al. |
| 5,013,312 | A | * | 5/1991 | Parins et al. .................... 606/37 |

(Continued)

FOREIGN PATENT DOCUMENTS

| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Michael Peffley
*Assistant Examiner* — Daniel Fowler (57) ABSTRACT

An end effector assembly for use with an electrosurgical instrument is provided. The end effector assembly includes a pair of opposing jaw members configured to grasp tissue therebetween, at least one jaw member adapted to connect to a source of electrosurgical energy to seal tissue disposed between jaw members during a sealing process. At least one of the jaw members includes an activator configured to selectively impart mechanical perturbations to the at least one jaw member during the sealing process.

11 Claims, 4 Drawing Sheets

(56) References Cited

U.S. PATENT DOCUMENTS

| | | | |
|---|---|---|---|
| 5,211,646 A * | 5/1993 | Alperovich et al. ............ 606/23 |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| 5,891,094 A * | 4/1999 | Masterson et al. ............ 604/113 |
| D416,089 S | 11/1999 | Barton et al. |
| 6,051,010 A * | 4/2000 | DiMatteo et al. ............ 606/169 |
| D424,694 S | 5/2000 | Tetzlaff et al. |
| D425,201 S | 5/2000 | Tetzlaff et al. |
| H1904 H | 10/2000 | Yates et al. |
| 6,174,309 B1 * | 1/2001 | Wrublewski et al. ............ 606/45 |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,723,092 B2 * | 4/2004 | Brown et al. .................. 606/41 |
| D493,888 S | 8/2004 | Reschke |
| 6,773,409 B2 * | 8/2004 | Truckai et al. ..................... 601/2 |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,618 B2 | 8/2006 | Couture et al. |
| 7,101,371 B2 | 9/2006 | Dycus et al. |
| 7,101,372 B2 | 9/2006 | Dycus et al. |
| D531,311 S | 10/2006 | Guerra et al. |
| 7,115,139 B2 | 10/2006 | McClurken et al. |
| D533,274 S | 12/2006 | Visconti et al. |
| D533,942 S | 12/2006 | Kerr et al. |
| D535,027 S | 1/2007 | James et al. |
| 7,156,846 B2 | 1/2007 | Dycus et al. |
| 7,166,103 B2 * | 1/2007 | Carmel et al. .................. 606/41 |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| 7,267,677 B2 | 9/2007 | Johnson et al. |
| 7,270,660 B2 | 9/2007 | Ryan |
| 7,300,447 B2 * | 11/2007 | Eliachar et al. ................ 606/170 |
| 7,329,257 B2 * | 2/2008 | Kanehira et al. ................ 606/52 |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,517,348 B2 * | 4/2009 | Vetter et al. ..................... 606/45 |
| 7,582,087 B2 | 9/2009 | Tetzlaff et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 2003/0073991 A1 | 4/2003 | Francischelli |
| 2004/0064151 A1 | 4/2004 | Mollenauer |
| 2004/0254607 A1 | 12/2004 | Wittenberger et al. |
| 2008/0132887 A1 * | 6/2008 | Masuda et al. ................. 606/37 |
| 2009/0254080 A1 | 10/2009 | Honda |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.

(56) References Cited

OTHER PUBLICATIONS

U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Towmey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington; D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.

(56) References Cited

OTHER PUBLICATIONS

Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 12168223.1 dated Aug. 14, 2012.

\* cited by examiner

DESTRUCTION OF VESSEL WALLS FOR ENERGY-BASED VESSEL SEALING ENHANCEMENT

BACKGROUND

1. Technical Field

The present disclosure relates to electrosurgical instruments used for open and endoscopic surgical procedures for sealing or fusing tissue. More particularly, the present disclosure relates to a bipolar forceps for sealing vessels, vascular tissues and soft tissues by applying mechanical vibrations and/or acoustic vibrations to destroy vessel walls and facilitate extraction of collagen and elastin during an electrosurgical procedure.

2. Background of the Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can cauterize, coagulate/desiccate and/or simply reduce or slow bleeding, by controlling the intensity, frequency and duration of the electrosurgical energy applied between the electrodes and through the tissue.

Certain surgical procedures require more than simply cauterizing tissue and rely on the combination of clamping pressure, electrosurgical energy and gap distance to "seal" tissue, vessels and certain vascular bundles. More particularly, vessel sealing or tissue sealing utilizes a unique combination of radiofrequency (RF) energy, clamping pressure and precise control of gap distance (i.e., distance between opposing jaw members when closed about tissue) to effectively seal or fuse tissue between two opposing jaw members or sealing plates. Vessel or tissue sealing is more than "cauterization", which involves the use of heat to destroy tissue (also called "diathermy" or "electrodiathermy"). Vessel sealing is also more than "coagulation", which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

Energy based vessel sealing consists of a few steps. During a vessel sealing procedure, opposing vessel walls are moved closer together. Then, the inner layer of the vessel walls that normally prevent adhesion of the vessel walls are destroyed. Elastin and collagen are released, mixed and exposed to energy to seal the vessel. Moving the vessel walls together, destruction of the inner layer of the vessel walls and releasing and mixing of collagen are traditionally achieved by pressurizing vessels between jaws. Destruction of the inner layer of the vessel wall requires application of a significant amount of force. If the vessel is located in a relatively thick layer of the tissue, the significant amount of force may damage and even break the upper tissue layers before sealing is completed.

SUMMARY

In an embodiment of the present disclosure, an end effector assembly is provided. The end effector assembly includes a pair of opposing jaw members configured to grasp tissue therebetween, at least one jaw member adapted to connect to a source of electrosurgical energy to effectively seal tissue disposed between jaw members during a sealing process. At least one of the jaw members includes an activator configured to selectively impart mechanical perturbations to the at least one jaw member during the sealing process.

In another embodiment of the present disclosure, an electrosurgical instrument for sealing tissue is provided. The electrosurgical instrument may include at least one shaft that supports an end effector assembly at a distal end thereof, the end effector assembly including a pair of opposing jaw members, at least one of the jaw members moveable relative to the other for grasping tissue therebetween, at least one of the jaw members adapted to connect to a source of electrosurgical energy to effectively seal tissue disposed between jaw members during a sealing process. At least one of the jaw members includes an activator configured to selectively impart mechanical perturbations to the at least one jaw member during the sealing process.

In yet another embodiment of the present disclosure, a method for sealing tissue using an end effector assembly having a pair of opposing jaw members wherein at least one jaw member has a member configured to impart mechanical perturbations to the at least one jaw member is provided. The method includes grasping tissue between the pair of opposing jaw members, activating the activator to move the at least one jaw member and applying electrosurgical energy to seal the tissue disposed between the jaw members.

The activator may provide a shearing force caused by the forward and/or backward movement of the at least one jaw member along a longitudinal axis. Alternatively, the activator may be a transducer that provides ultrasound to impart mechanical perturbations to the at least one jaw member.

BRIEF DESCRIPTION OF THE DRAWINGS

Objects and features of the presently disclosed systems and methods will become apparent to those of ordinary skill in the art when descriptions of various embodiments thereof are read with reference to the accompanying drawings, of which.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Electromagnetic energy is generally classified by increasing frequency or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3\times10^8$ cycles/second) to 300 gigahertz (GHz) ($3\times10^{11}$ cycles/second). As used herein, the term "RF" generally refers to electromagnetic waves having a lower frequency than microwaves. As used herein, the term "ultrasound" generally refers to cyclic sound pressure with a frequency greater than the upper limit of human hearing. The terms "tissue" and "vessel" may be used interchangeably since it is believed that the present disclosure may be employed to seal and cut tissue or seal and cut vessels utilizing the same principles described herein.

As will be described in more detail below with reference to the accompanying figures, the present disclosure is directed to the use mechanical or acoustic vibrations to destroy vessel walls and intensify release of collagen and elastin.

Figure 1:
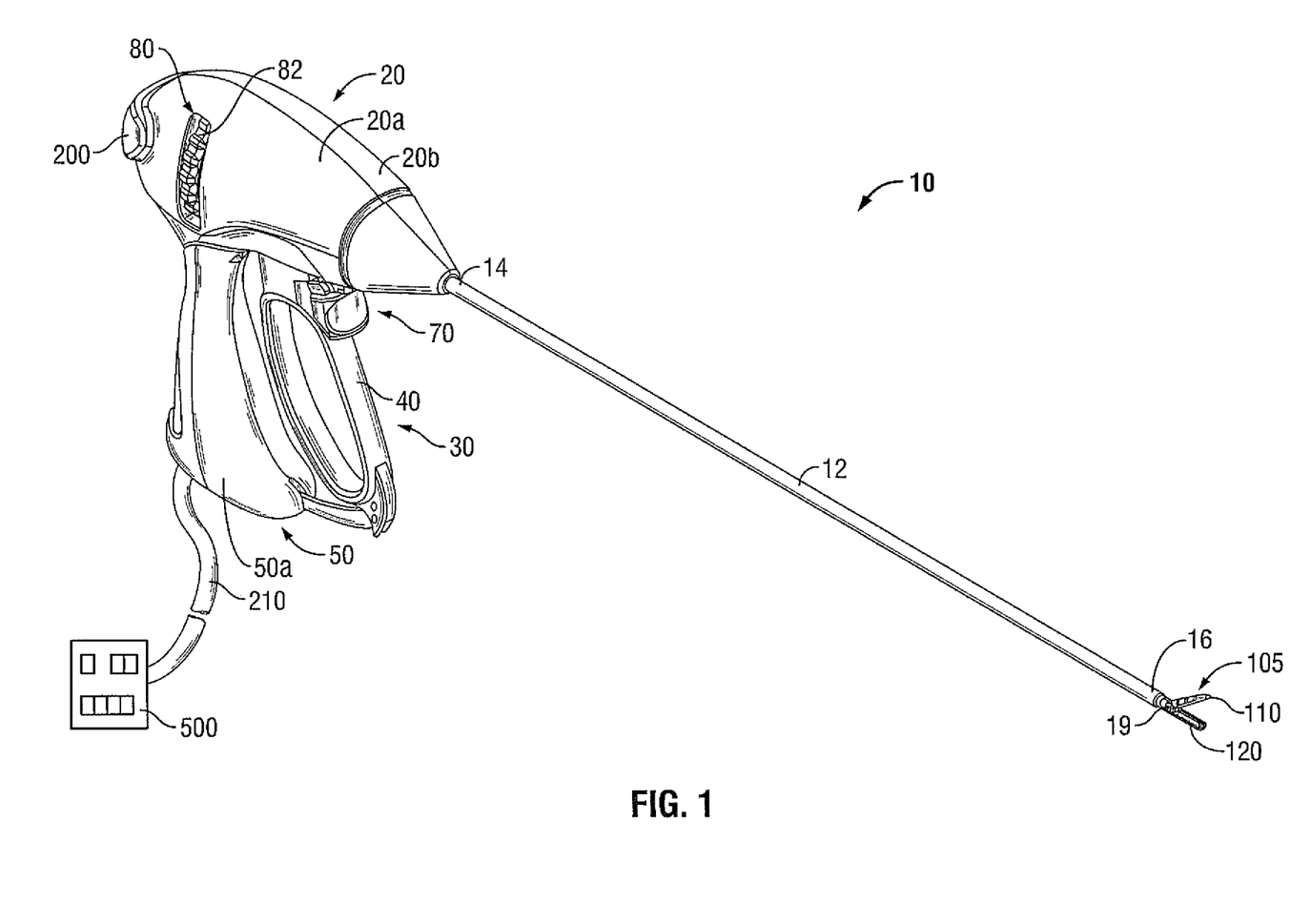
FIG. 1 is a right, perspective view of an endoscopic bipolar forceps having a housing, a shaft and a pair of jaw members affixed to a distal end thereof; the jaw members including an electrode assembly disposed therebetween.
Figure 2:
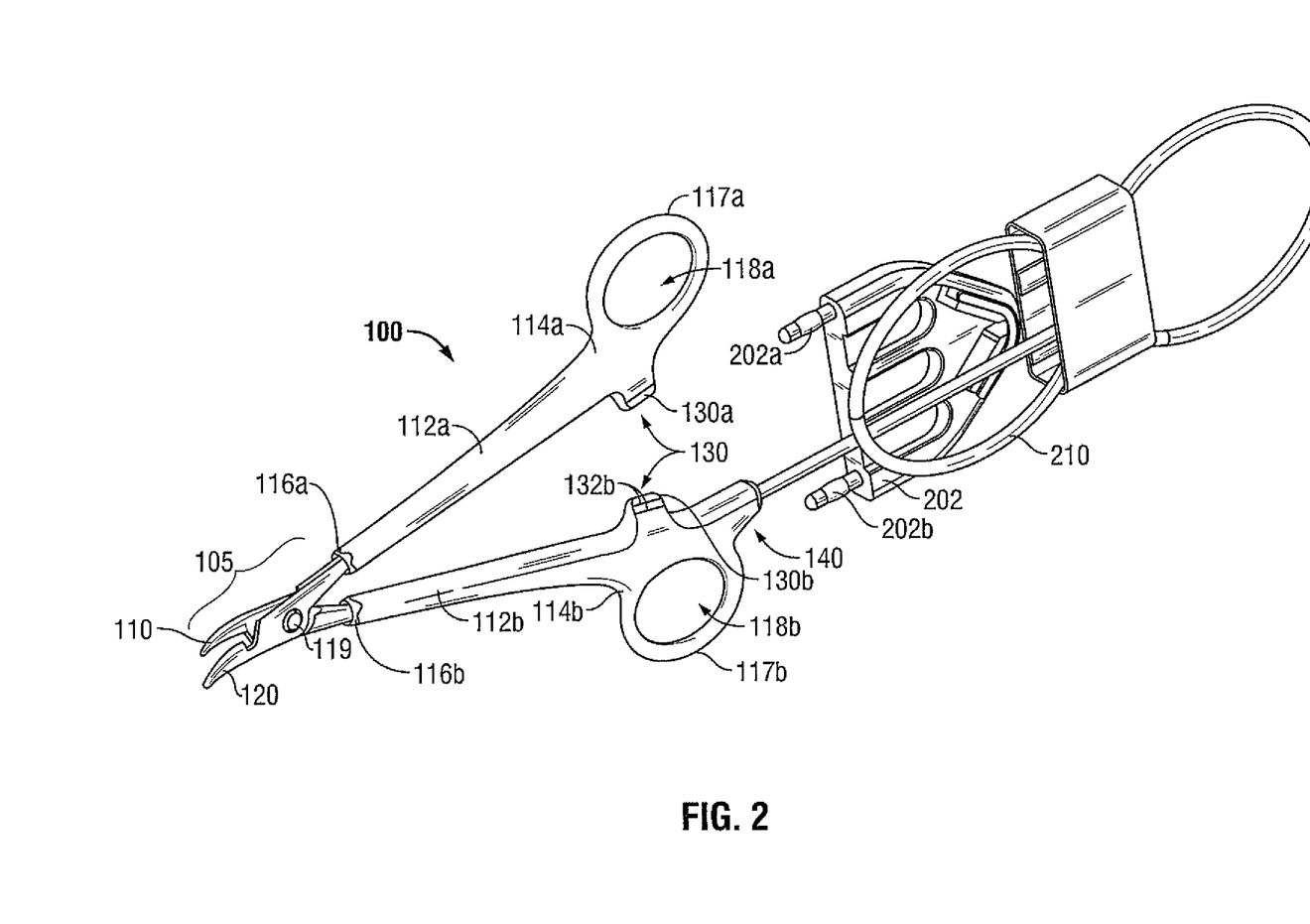
FIG. 2 is a left, perspective view of an open bipolar forceps showing a pair of first and second shafts each having a jaw member affixed to a distal end thereof with an electrode assembly disposed therebetween.

Referring now to FIGS. 1 and 2, FIG. 1 depicts a bipolar forceps 10 for use in connection with endoscopic surgical procedures and FIG. 2 depicts an open forceps 100 contemplated for use in connection with traditional open surgical procedures. For the purposes herein, either an endoscopic instrument or an open instrument may be utilized with the electrode assembly described herein. Different electrical and mechanical connections and considerations may apply to each particular type of instrument; however, the aspects with respect to the electrode assembly and its operating characteristics remain generally consistent with respect to both the open or endoscopic designs.

FIG. 1 shows a bipolar forceps 10 for use with various endoscopic surgical procedures and generally includes a housing 20, a handle assembly 30, a rotating assembly 80, a knife actuator 70 and an electrode assembly 105 having opposing jaw members 110 and 120 that mutually cooperate to grasp, seal and divide tubular vessels and vascular tissue. The jaw members 110 and 120 are connected about pivot pin 19, which allows the jaw members 110 and 120 to pivot relative to one another from the first to second positions for treating tissue. More particularly, forceps 10 includes a shaft 12 that has a distal end 16 configured to mechanically engage the electrode assembly 105 and a proximal end 14 that mechanically engages the housing 20. The shaft 12 may include one or more suitable mechanically-engaging components that are designed to securely receive and engage the electrode assembly 105 such that the jaw members 110 and 120 are pivotable relative to one another to engage and grasp tissue therebetween.

The proximal end 14 of shaft 12 mechanically engages the rotating assembly 80 to facilitate rotation of the electrode assembly 105. In the drawings and in the descriptions that follow, the term "proximal", as is traditional, will refer to the end of the forceps 10 that is closer to the user, while the term "distal" will refer to the end that is further from the user. Details relating to the mechanically cooperating components of the shaft 12 and the rotating assembly 80 are described in commonly-owned U.S. patent application Ser. No. 10/460,926, now U.S. Pat. No. 7,156,846, entitled "VESSEL SEALER AND DIVIDER FOR USE WITH SMALL TROCARS AND CANNULAS" filed on Jun. 13, 2003.

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the electrode assembly 105 as explained in more detail below. Movable handle 40 and knife actuator 70 are of unitary construction and are operatively connected to the housing 20 and the fixed handle 50 during the assembly process. Housing 20 is constructed from two component halves 20a and 20b that are assembled about the proximal end 14 of shaft 12 during assembly. Switch assembly 200 is configured to selectively provide electrical energy to the electrode assembly 105.

As mentioned above, electrode assembly 105 is attached to the distal end 16 of shaft 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Referring now to FIG. 2, an open forceps 100 includes a pair of elongated shaft portions 112a and 112b each having a proximal end 114a and 114b, respectively, and a distal end 116a and 116b, respectively. The forceps 100 includes jaw members 120 and 110 that attach to distal ends 116a and 116b of shafts 112a and 112b, respectively. The jaw members 110 and 120 are connected about pivot pin 119 that allows the jaw members 110 and 120 to pivot relative to one another from the first to second positions for treating tissue. The electrode assembly 105 is connected to opposing jaw members 110 and 120 and may include electrical connections through or around the pivot pin 119. Examples of various electrical connections to the jaw members are shown in commonly-owned U.S. patent application Ser. Nos. 10/474,170, 10/284,562 10/472,295, 10/116,944 and 10/179,863, now U.S. Pat. Nos. 7,582,087, 7,267,677, 7,101,372, 7,083,618 and 7,101,371 respectively.

Each shaft 112a and 112b includes a handle 117a and 117b disposed at the proximal end 114a and 114b thereof that each define a finger hole 118a and 118b, respectively, therethrough for receiving a finger of the user. As can be appreciated, finger holes 118a and 118b facilitate movement of the shafts 112a and 112b relative to one another, which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween. A ratchet 130 may be included for selectively locking the jaw members 110 and 120 relative to one another at various positions during pivoting.

More particularly, the ratchet 130 includes a first mechanical interface 130a associated with shaft 112a and a second mating mechanical interface 130b associated with shaft 112b. Each position associated with the cooperating ratchet interfaces 130a and 130b holds a specific, i.e., constant, strain energy in the shaft members 112a and 112b, which, in turn, transmits a specific closing force to the jaw members 110 and 120. The ratchet 130 may include graduations or other visual markings that enable the user to easily and quickly ascertain and control the amount of closure force desired between the jaw members 110 and 120.

As best seen in FIG. 2, forceps 100 also includes an electrical interface or plug 200 that connects the forceps 100 to a source of electrosurgical energy, e.g., an electrosurgical generator similar to generator 500 shown in FIG. 1. Plug 202 includes at least two prong members 202a and 202b that are dimensioned to mechanically and electrically connect the forceps 100 to the electrosurgical generator 500 (See FIG. 1). An electrical cable 210 extends from the plug 202 and securely connects the cable 210 to the forceps 100. Cable 210 is internally divided within the shaft 112b to transmit electrosurgical energy through various electrical feed paths to the electrode assembly 105.

One of the shafts, e.g. 112b, includes a proximal shaft connector/flange 140 that is designed to connect the forceps 100 to the source of electrosurgical energy such as electrosurgical generator 500. More particularly, flange 140 mechanically secures electrosurgical cable 210 to the forceps 100 such that the user may selectively apply electrosurgical energy as needed.

Figure 3:
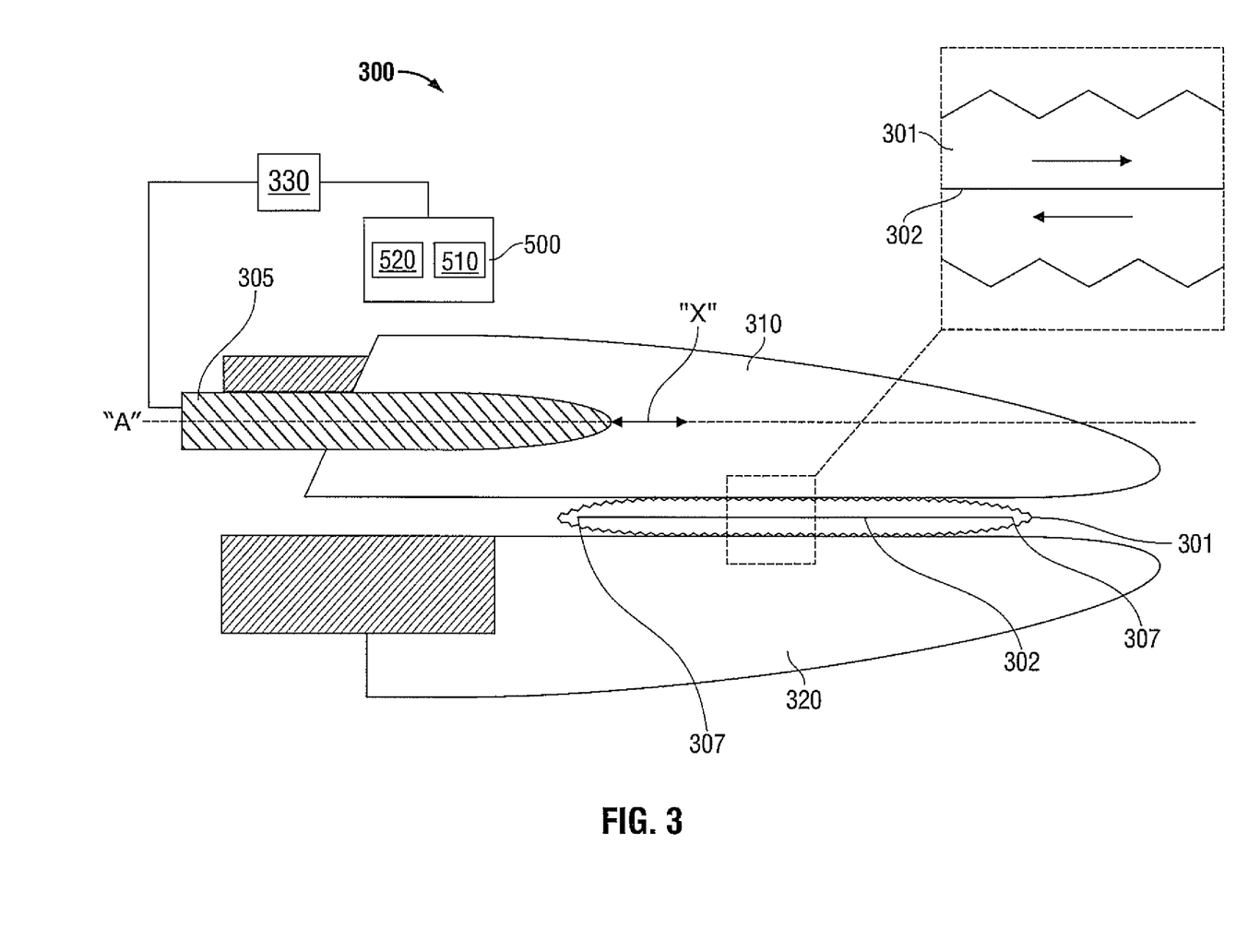
FIG. 3 is a schematic view of an end effector assembly having a pair of jaw members according to an embodiment of the present disclosure.

Referring to FIG. 3, an end effector assembly according to an embodiment of the present disclosure is shown generally as end effector 300. End effector assembly 300 is substantially similar to electrode assembly 105 shown at the distal end of forceps 10 and/or forceps 100. End effector assembly 300 includes an upper jaw member 310 and lower jaw member 320. Jaw members 310 and 320 are used to grasp vessel 301 therebetween. Jaw members 310 and 320 may include one or more electrodes (not shown) to provide RF energy to vessel 301 to seal vessel 301.

As shown in FIG. 3, jaw member 310 includes an activator 305 that imparts mechanical perturbations to jaw member 310. Activator 305 may be mechanically or magnetically coupled to jaw member 310. For example, activator 305 may have an adhesive applied thereon before inserted into jaw member 310 or activator 305 may be soldered onto jaw member 310. Additionally, activator 305 may have a mechanical interface, e.g., a notch or protrusion that cooperates with a corresponding mechanical interface in jaw member 310. Although not shown, activator 305 may also be included in jaw member 320 or both jaw members 310 and 320. Activator 305 provides forward and/or backward movement of jaw member 310 along a longitudinal axis "A" defined therethrough relative to jaw member 320 (see arrow "X" on FIG. 3). The forward and/or backward movements of jaw members 310 and 320 relative to each other deforms vessel 301 due to compressing and shearing forces. The application of the compressing and shearing forces leads to the destruction of inner layer 302 of vessel 301 which releases and mixes elastin and/or collagen during a sealing cycle.

The shearing forces are produced by movement of jaw member 310 along longitudinal axis "A". The maximum deformation of inner layer 302 occurs where the curvature of the compressed vessel is at its maximum (307). The shearing forces extend area 307 and accelerate destruction of inner layer 302 as well as accelerating the release of elastin and collagen disposed therein. Additionally, friction between inner walls of vessel 301 created in the tissue by the forward and backward movements of jaw members 320 contributes to the destruction of inner layer 302.

Activator 305 may be mechanically, electrically, or magnetically coupled to an actuator 330. Actuator 330 may be a motor, electromagnet or any other device that imparts motion to activator 305, thereby causing activator 305 to move in a longitudinal direction along axis "A". Actuator 330 may be controlled by generator 500 or may be controlled by a user.

Generator 500 includes a memory 510 and a processor 520. Memory 510 may store a program or routine for performing a vessel sealing procedure that is executed by processor 520. Generator 500 provides electrosurgical energy to end effector assembly 300 according to the program or routine stored in memory 510. Generator 500 also controls actuator 330 according to a program or routine stored in memory 510. To avoid damaging outer tissue layers before sealing is completed, generator 500 may control actuator 330 to limit the movement of activator 305.

Figure 4:
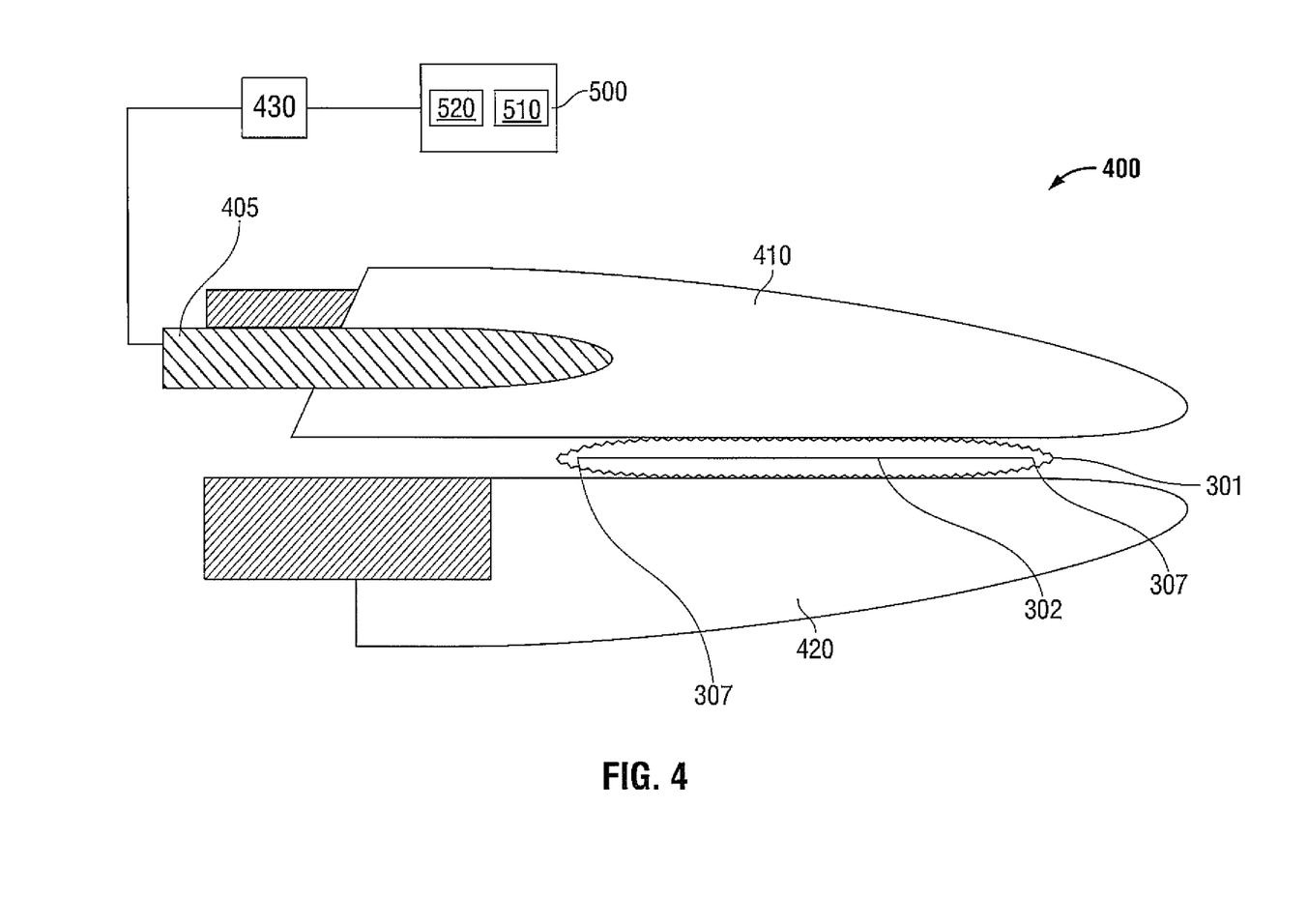
FIG. 4 is a schematic view of an end effector assembly having a pair of jaw members according to another embodiment of the present disclosure.

Referring to FIG. 4, an end effector assembly according to another embodiment of the present disclosure is shown generally as 400. End effector assembly 400 includes upper jaw member 410 and lower jaw member 420. Upper jaw member 410 includes a transducer 405 that receives electrical energy from energy source 430 and converts the electrical energy into ultrasound to impart mechanical perturbations to jaw member 410, Energy source 430 may be a stand-alone unit, built into the forceps 10 or forceps 100 or may be included in generator 500.

Transducer 405 may be mechanically or magnetically coupled to jaw member 410. For example, transducer 405 may have an adhesive applied thereon before inserted into jaw member 410 or transducer 405 may be soldered onto jaw member 410. Additionally, transducer 405 may have a mechanical interface, e.g., a notch or protrusion that cooperates with a corresponding mechanical interface in jaw member 410.

Ultrasound provided by transducer 405 causes periodic movement in upper jaw member 410 resulting additional heating and destruction of inner layer 302 of vessel 301. Transducer 405 may be located in upper jaw member 310, lower jaw member 320 or both jaw members.

As described above, generator 500 includes a memory 510 and a processor 520. Memory 510 may store a program or routine for performing a vessel sealing procedure that is executed by processor 520. Generator 500 provides electrosurgical energy to end effector assembly 400 according to the program or routine stored in memory 510. Generator 500 also controls energy source 430 according to a program or routine stored in memory 510. To avoid damaging outer tissue layers before sealing is completed, generator 500 may control energy source 430 to limit the amplitude of periodic movements of transducer 405.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. An end effector assembly for use with an instrument for sealing tissue, the end effector assembly comprising:
    a pair of opposing jaw members configured to grasp tissue therebetween, at least one jaw member adapted to connect to a source of electrosurgical energy to seal tissue disposed between jaw members during a sealing process, the at least one jaw member having a substantially planar electrode; and
    an activator coupled to at least one jaw member and configured to selectively impart sub-ultrasonic mechanical perturbations to the at least one jaw member during the sealing process,
    wherein the activator provides a shearing force caused by the forward and/or backward movement of the at least one jaw member along a longitudinal axis defined therethrough.

2. The end effector assembly of claim 1, wherein the activator is magnetically coupled to the at least one jaw member.

3. The end effector assembly of claim 1, wherein the activator is mechanically coupled to the at least one jaw member.

4. An electrosurgical instrument, comprising:
    at least one shaft that supports an end effector assembly at a distal end thereof, the end effector assembly including a pair of opposing jaw members, at least one of the jaw members moveable relative to the other for grasping tissue therebetween, at least one of the jaw members adapted to connect to a source of electrosurgical energy to seal tissue disposed between jaw members during a sealing process, the at least one jaw member having a substantially planar electrode; and an activator coupled to at least one jaw member and configured to selectively impart sub-ultrasonic mechanical perturbations to the at least one jaw member during the sealing process, wherein the activator provides a shearing force caused by the forward and/or backward movement of the at least one jaw member along a longitudinal axis defined therethrough.

5. The electrosurgical instrument of claim 4, further comprising an actuator that is coupled to the activator.

6. The electrosurgical instrument of claim 5, wherein the actuator is a motor.

7. The electrosurgical instrument of claim 5, wherein the actuator is an electromagnet.

8. The electrosurgical instrument of claim 5, wherein the actuator is mechanically coupled to the activator.

9. The electrosurgical instrument of claim 5, wherein the actuator is magnetically coupled to the activator.

10. The electrosurgical instrument of claim 5, wherein the actuator is electrically coupled to the activator.

11. A method for sealing tissue using an end effector assembly having a pair of opposing jaw members moveable relative to one another for grasping tissue disposed therebetween wherein at least one jaw member having a substantially planar electrode includes an activator disposed therein, the method comprising:

grasping tissue between the pair of opposing jaw members;

activating the activator to impart sub-ultrasonic mechanical perturbations to the at least one jaw member thereby causing the at least one jaw member to move along a longitudinal axis defined therethrough; and applying electrosurgical energy to seal the tissue disposed between the jaw members.

* * * * *